United States Patent [19]
Binot

[11] Patent Number: 5,725,757
[45] Date of Patent: Mar. 10, 1998

[54] REACTOR FOR UV RADIATION FOR THE TREATMENT OF LIQUIDS

[75] Inventor: Patrick Binot, Bussy Saint-Martin, France

[73] Assignee: OTV Omnium de Traitements et de Valorisation (Societe Anonyme), St. Maurice Cedex, France

[21] Appl. No.: 586,486

[22] Filed: Jan. 16, 1996

[30] Foreign Application Priority Data

Jan. 16, 1995 [FR] France ............... 95 00616

[51] Int. Cl.[6] ...................... C02F 1/32
[52] U.S. Cl. ............... 210/85; 210/105; 210/177; 210/192; 210/195.1; 210/198.1; 210/205; 422/186.3; 250/431; 250/436
[58] Field of Search ............ 210/85, 103, 105, 210/149, 177, 192, 195.1, 198.1, 199, 205, 209; 422/186.3; 250/431, 436, 437

[56] References Cited

U.S. PATENT DOCUMENTS

| | | | |
|---|---|---|---|
| 2,732,502 | 1/1956 | Darney | 250/431 |
| 4,017,734 | 4/1977 | Ross | 250/431 |
| 4,141,830 | 2/1979 | Last | 210/192 |
| 4,156,652 | 5/1979 | Wiest | 250/436 |
| 4,201,917 | 5/1980 | Graentzel | 250/431 |
| 4,273,660 | 6/1981 | Beitzel | 210/760 |
| 4,400,270 | 8/1983 | Hillman | 210/105 |
| 5,124,131 | 6/1992 | Wekhof | 422/186.3 |
| 5,133,945 | 7/1992 | Hallett | 422/186.3 |
| 5,160,040 | 11/1992 | Odawara et al. | 210/195.1 |
| 5,332,388 | 7/1994 | Schuerch et al. | 250/431 |

FOREIGN PATENT DOCUMENTS

| | | |
|---|---|---|
| 0 080 780 | 6/1983 | European Pat. Off. . |
| 0 202 820 | 11/1986 | European Pat. Off. . |
| 0 361 579 | 4/1990 | European Pat. Off. . |
| 0 470 518 | 2/1992 | European Pat. Off. . |
| 34 14 870 | 10/1985 | Germany . |
| 39 24 349 | 1/1991 | Germany . |
| WO 88/04281 | 6/1988 | WIPO . |
| WO 91/09673 | 7/1991 | WIPO . |
| WO 92/22502 | 12/1992 | WIPO . |
| WO 93/02965 | 2/1993 | WIPO . |

*Primary Examiner*—Neil McCarthy
*Assistant Examiner*—Theodore M. Green
*Attorney, Agent, or Firm*—Merchant Gould Smith Edell Welter & Schmidt

[57] ABSTRACT

The invention relates to a reactor for UV radiation for the disinfection of liquids comprising at least one high or medium pressure UV emitter (1) arranged coaxially inside a protective sheath (2) transparent to UV, the assembly formed by the emitter and the sheath being located coaxially inside a tubular shell (3) whose internal face reflects at least 30% of the incident UV at 250 to 260 nm coming from the emitter (1), the liquid to be treated transiting according to a flow pipe in an active chamber (4) defined by the internal face of the shell (3) and the external face of the sheath (2), the reactor being characterized in that it is connected to washing means (30) of the active chamber (4) including means making it possible to make a cleaning liquid circulate in the active chamber (4) and air injection means (8) provided upstream from the active chamber (5) making it possible to improve the turbulence of the cleaning liquid during washing.

13 Claims, 4 Drawing Sheets

REACTOR FOR UV RADIATION FOR THE TREATMENT OF LIQUIDS

BACKGROUND OF THE INVENTION

This invention relates to the disinfection of liquids, in particular drinking water or waste water, contaminated by micro-organisms, with the help of high-pressure or medium-pressure UV lamps.

In particular, the invention relates to various original arrangements allowing the improvement of the efficiency of high pressure or medium pressure UV disinfection.

The DNA of micro-organisms submitted to bombardment by UV photons undergoes modifications which can prevent replication. The statistical proportion of micro-organisms of a given type thus inactivated within a given population is proportional to the UV dose (product of intensity of radiation and time of exposure) received by the population under consideration. Certain wavelengths, in particular the wavelength of 254 nm, have a better germicidal efficiency than the others.

There are two main types of emitters of UV radiation commercially available at present. Low-pressure mercury-vapour UV lamps (LP-UV lamps) which have the advantage of emitting quasi-monochromatic radiation of 254 nm, that is the optimal wavelength for germicidal efficiency, nonetheless have the inconvenience of being limited in unit power. LP-UV lamps commercially available at present are in the general range of 50–200 watts. Thus a large number of lamps must usually be installed in order to treat an average flow of waste water.

High or medium pressure mercury-vapour UV lamps (HP-UV or MP-UV) have an emission spectrum which is broader, and thus have lower germicidal efficiency, but their unit power can be very high (lamps of 3 kW, 10 kW and even 100 kW are available at present). It is to be noted that within the framework of the present description, under the terms high or medium pressure UV emitters are included UV emitters with power of at least 500 W, and generally from 3 to 100 kW.

Basically, two types of UV reactors are used in the water treatment industry.

On the one hand, reactors of the open type, or in a channel, in which the liquid flowing under the force of gravity with its surface free passes between a multitude of lamps regularly arranged parallel to each other in the channel (in vertical, horizontal or inclined positions).

On the other hand, reactors of the closed type, generally under pressure, in which the water to be treated circulates in a chamber containing one or several UV emitters parallel to the axis of the chamber and arranged with a constant spacing in a given section of the chamber. Such reactors of the closed type can in particular be constituted of a UV emitter placed coaxially inside a protective sheath transparent to UV, the ensemble comprised by said emitter and said sheath being itself placed coaxially inside a tubular shell, the liquid to be treated transiting in a flow pipe in an active chamber defined by the internal face of said shell and the external face of said sheath. It is more precisely to this type of closed reactor that the invention is intended to be applied.

Such reactors are described in particular in U.S. Pat. No. 4,273,660, EP-A-3 924 349 or again in WO 93/02965.

It is to be noted that reactors of this type can comprise several emitters and several active chambers, each emitter being arranged coaxially inside a protective sheath transparent to UV and each emitter supplying a single active chamber.

The use of HP or MP-UV lamps is tending to assert itself in the domain of the treatment of drinking water, since the compactness, simplicity and economy of investment obtained by using HP-UV lamps in closed reactors more than compensates for the increase in electricity consumption due to the lower germicidal efficiency of HP-UV or MP-UV lamps compared with LP-UV lamps.

In the domain of waste water, the most frequently used technology at present remains LP-UV technology in open reactors, as described in particular in European Patent Applications EP-A-361 579A1 and EP-A-80 780. In fact the waste water usually treated presents low transmission coefficients (40% to 60% on a 1 cm wave) thus giving greater importance to the consumption of electricity than in the case of drinking water. LP-UV lamps, which provide higher germicidal efficiency for the radiation produced, are thus at present often preferred for treating waste water.

However, HP or MP-UV lamps have many potential advantages which could make them more suitable than LP-UV lamps:

- better adaptation to automatic regulation of the power radiated according to requirements (LP lamps work on an all-or-nothing basis, while HP/MP lamps can be regulated in power steps or continuously);
- better adaptation to automated cleaning, in practice LP-UV lamps needing a periodic manual washing which is manpower consuming and a potential source of breakage of lamps and quartz sheaths;
- better control of the hydraulics of the fluid to be treated is possible in the case of single HP (MP)-UV lamps, coaxial with the reactor, in comparison with the hydraulics observed in multi-lamp channels. Hydraulics control is in fact essential in order to ensure a statistically identical dose of radiation for each particle swept along by the fluid being treated.

However, the HP (or MP) -UV reactors with coaxial lamps commercially available and described in the literature do not allow minimization of the energy loss linked to the soiling of the UV reactor elements.

Until now, the minimization linked to soiling could only be obtained using a protective plastic film, for example by applying on this sheath a thin layer of fluoroethylene propylene (FEP), as suggested by patent WO 91/09673 of 11.07.91 or by the patent WO 88/04281 of 9.12.87, or by using scraper mechanisms, more or less complicated and liable to break down, for the periodic cleaning of the surface of the UV transparent tube protecting the UV reactor, such as that proposed by the patent WO 92/22502. These films and scrapers are usually not very efficient against mineral deposits such as calcium carbonate and are thus not well adapted to the treatment of liquids relatively heavily loaded with impurities such as, in particular, waste water.

Moreover, reactors of the closed type also do not make it possible to obtain uniformity of time spent in the reactor by limiting efficiently and at a low equipment cost the serious hydraulic short circuits caused by the off-centre entry and exit of the liquid to be treated in the reactor.

SUMMARY OF THE INVENTION

The prime object of the present invention is to improve the efficiency of reactors with coaxial HP-UV or MP-UV lamps in such a way as to make them economically interesting for the treatment of such liquids, by delaying to a maximum the soiling of the active chamber and the sheath protecting the UV emitter of such a reactor by permitting automatic cleaning up when this is necessary.

Another object of the invention is to improve the germicidal efficiency of the HP or MP-UV disinfection devices using a lamp coaxial with a tube by optimizing the irradiation dose of each particle of the liquid treated in such a reactor and by improving the turbulence of this liquid.

Up until now, the techniques used to produce turbulence of the liquid in the reactor have consisted in homogenizing the doses of liquid applied by radial mixing, by interposing various devices of the diaphragm or baffle type etc., as described in particular in the Patent Application EP-A-202 820.

These various objects, together with others which will appear later, can be achieved thanks to the invention which relates to a UV irradiation reactor, of the closed type, for the disinfection of liquids comprising at least one high or medium-pressure UV emitter arranged coaxially inside a protective sheath transparent to UV radiation, the assembly formed by said emitter and said sheath being placed coaxially inside a tubular shell whose internal face reflects at least 30% of the incident UV at 250 to 260 nm coming from said emitter, the liquid to be treated transiting in a flow pipe in an active chamber defined by said internal face of said shell and the external face of said sheath, said reactor being characterized in that it is linked to the washing means of said active chamber including means allowing the circulation of a cleaning liquid in said active chamber and to air injecting means provided upstream from said active chamber in particular allowing the improvement of the turbulence of said cleaning liquid during washing.

Utilization of a cleaning liquid in reactors in a channel was in fact inconceivable because of their open configuration. Concerning reactors of the closed type, the use of scrapers and/or cleaning liquids was known.

In the invention, said reactor also includes air injecting means for improving the turbulence of the cleaning liquid during washing. The air thus used helps "to assist" the cleaning liquid without itself possessing any marked cleaning effect.

It should be noted that the use of air injection had also never been envisaged within the framework of reactors of the closed type for the purpose of improving the efficiency of a cleaning liquid. Only the document U.S. Pat. No. 4,273,660 advocated the injection of air having transited the space provided between the emitter and the protective sheath, and thus containing a certain quantity of ozone, with the sole object of accentuating the disinfection of the water transiting the active chamber.

Such washing means can be implemented up according to a time schedule but preferably, the reactor according to the invention will include means for automatically activating the washing means. These automatic activation means could preferably include a UV sensor provided at the level of the shell of the reactor and allowing the evaluation of UV transmission of the liquid wave present in the active chamber of the reactor and the degree of soiling in this chamber.

It is also preferred that said means of washing include means for recycling said cleaning liquid.

It is also advantageous that such washing means also include concentration readjusting means thereof.

It is also preferred that the reactor includes automatic means of activation of said washing means.

It is also preferred that said means of activation include a UV sensor provided at the level of said shell of the reactor.

It is also advantageous that the reactor comprises means for heating said cleaning liquid.

As described above, the internal face of the shell reflects at least 30% of the incident UV at 250 to 260 nm coming from the emitter.

Typically, according to the materials used to make the internal wall of this shell, such reflection will be between 35 and 60%.

The energy recuperated thanks to such feature is used for the disinfection of the flow parts which are furthest from the UV emitter, that is to say the flow parts which are the least irradiated. Thus the invention allows a complement of irradiation which makes it possible to improve the overall performance of the irradiation treatment.

In a preferred embodiment of the invention, said shell is made of stainless steel, preferably 304 L or 316 L and its internal face presents a mirror polish with grain between 100 and 350. In an unexpected fashion, it has in fact been noted that such stainless steels treated in this way allowed optimization of the energy of the reactor by cumulating the following features:

better resistance to soiling by organic matters contained in the liquid to be treated (and greater ease of cleaning), allowing the efficiency of the disinfection to be maintained for a longer period of time;

a reflection coefficient of the clean surface k about equal to 0.40 and approximately double than that obtained on non-polished stainless steel sheet, making it possible to recuperate more than 40% of the incident UV energy (at wavelengths of around 250 to 260 nm).

The use of a stainless steel shell whose internal wall presents a mirror polish with grain greater than 100 and the use of a cleaning liquid injection means assisted by air thus combine through synergy to give better efficiency to the reactor according to the invention.

It should be noted that other metals apart from stainless steel also give good reflection results, such as aluminium, which however has a higher tendency to corrosion by the liquids treated, or chromium.

In another embodiment of the invention, said internal face of said shell can also be constituted of a metallic layer formed by electroplating.

Moreover, advantageously, the reactor according to the invention has dimensions so as to provide, in the considered flow of liquid to be treated, a Reynolds number which is higher than 6,000 in the internal flow pipe of the reactor. The dose received by a particle transiting the reactor at a distance r from the emitter is essentially a function of this distance r according to the Beer-Lambert law. According to the invention, the dimensions of the reactor are thus designed so that each element of the fluid to be treated receives a similar dose of irradiation, making it possible to ensure a turbulent flow of a Reynolds number greater than 6,000. Typically, the Reynolds number of the flowing fluid will thus be between 10,000 and 60,000.

Equally advantageously, said reactor has means making for submitting the liquid to be treated entering said active chamber to a symmetric loss of load at least three times higher than the asymmetric loss of load observed for the liquid to be treated before its entry into said reactor.

Such loss of load helps to obtain a homogeneous distribution of the fluid to be treated in the active chamber of the reactor and thus good homogeneity of the length of stay of each entering particle, which makes it possible to further optimize the operation of the reactor.

In an embodiment of the invention, such loss of load is obtained thanks to an injection chamber provided coaxially to one extremity of said shell and at least one inlet nozzle allowing the introduction—preferably tangential—of the liquid to be treated into said reactor via said injection chamber, said injection chamber communicating with said active chamber through a circular slot.

In another embodiment, the reactor is intended to be placed in a chamber of greater dimensions limiting the effect of the asymmetric arrival of the liquid to be treated, and in its lower part has an annular space between said tubular shell and said protective sheath and separated from said active chamber by a narrow passage.

Advantageously, the reactor comprises injection means for at least one reagent able to complete the disinfection and/or to detoxify said liquid, said injection means being provided upstream from said active chamber. These injection means for at least one reagent (ozone, oxygenated water ...) can be formed by the air injection means cited above.

Advantageously, said reactor includes power regulation means for said emitter operating as a function of one or several parameters chosen among the group constituted by the flow of treated liquid, the UV transmission of the treated liquid, and the time which has passed since the last washing.

The invention also relates to a method for using a reactor according to the invention characterized in that it consists in operating said emitter when the washing means are put into operation. Such method can extend the life span of the emitter.

Unexpectedly and curiously, it was also noted that the germicidal efficiency of a unit of energy consumed by an HP/MP UV emitter was even better, expressed in terms of the logarithmic reduction of the germs, when the emitter was used at low power compared with its nominal power.

Thus, if 10 emitters of 10 kW per unit are able to treat, for example, a peak flow of 1,000 cu.m. per hour of given waste water, it is more efficient to treat an average flow of 600 cu.m. per hour with 10 lamps operating at 6 kW per unit than with 6 emitters at their nominal power of 10 kW.

Consequently, the invention also covers a method for regulating a system of several HP/MP UV emitters according to which the power needed for the treatment of a given overall flow is obtained by dividing uniformly the total power necessary between the number of emitters available, rather than by using several emitters only at their maximum power.

It is understood that this method will only be applied, in the case of lower and lower flows, until the minimal unitary power acceptable for each emitter is reached.

BRIEF DESCRIPTION OF THE FIGURES

The invention, as well as the different advantages it represents, is better understood through the following description giving non-limiting examples of embodiments referring to the drawings in which.

DETAILED DESCRIPTION

Figure 1:
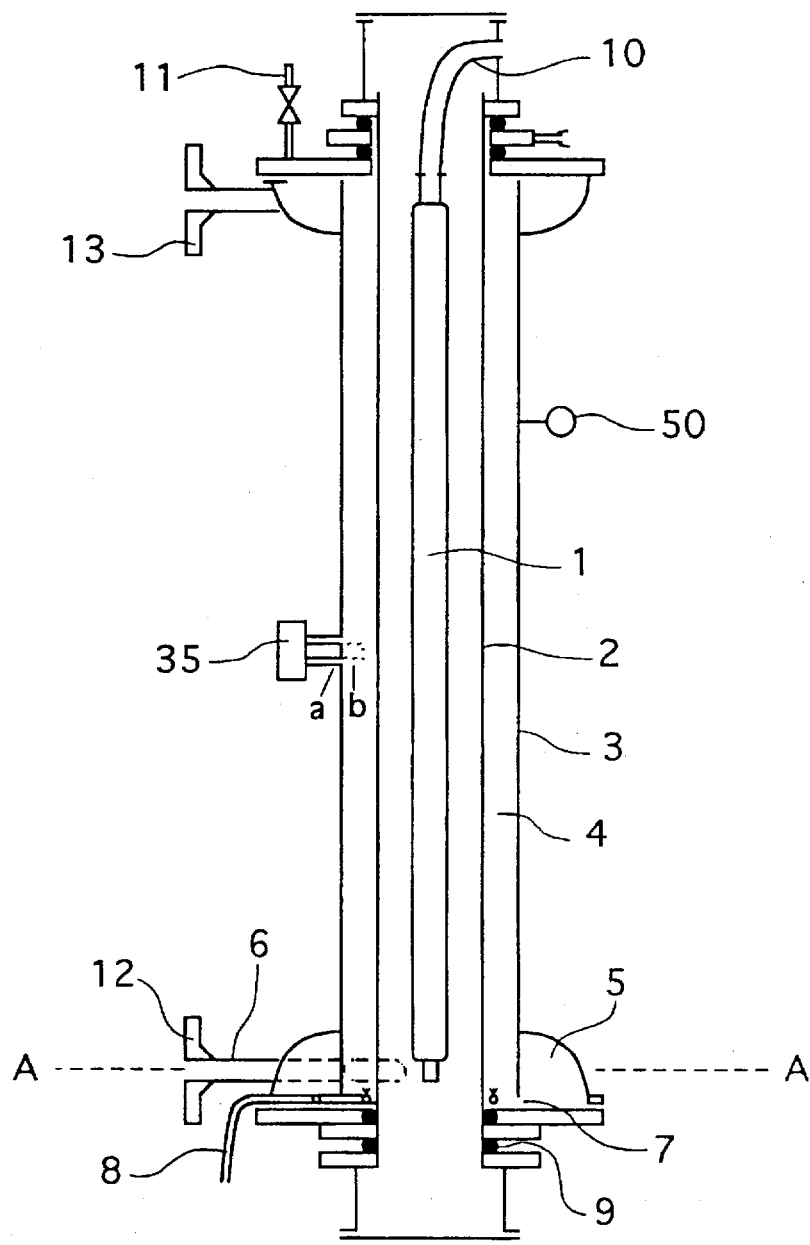
FIG. 1 shows a lateral view of a longitudinal section of a first embodiment of the invention.

According to FIG. 1, the UV irradiation reactor represented includes a medium-pressure UV lamp 1 of nominal power 6 kW located inside a protection sheath made of quartz (material transparent to UV) of external diameter 140 mm. The assembly comprising lamp 1 and its sheath 2 is placed inside a metallic shell 3 of internal diameter 200 mm and coaxial with it. The internal wall of the shell 3 and the external wall of the sheath 2 define an active chamber 4 inside which a liquid to be disinfected transits. This liquid enters the reactor through an inlet 12 situated at its foot and exits through an outlet 13 situated at the head of the reactor after being irradiated.

The dimensions of the active chamber 4 are determined in such a way as to allow the pipe flow of this liquid according to a wave of thickness 30 mm. It should be noted that in practice this thickness in other embodiments is generally of the order of 1 to 10 cm. Moreover, the length of irradiation permitted by the reactor shown is 1 meter, while its cleaning volume is about 30 liters.

In the case shown, the shell 3 is made of stainless steel 316 L internally polished to grade 150.

A sealing system with O-rings 9 ensures insulation, from the liquid medium, of the interior of the quartz sheath 2 and of the electrical supply of the lamp 1.

Figure 2:
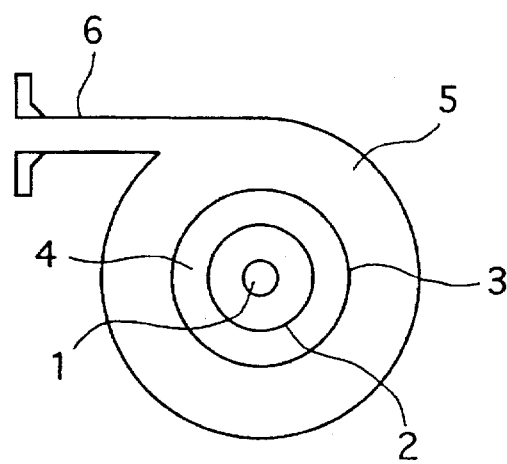
FIG. 2 shows a transversal section AA through the reactor shown in FIG. 1.

In the lower part of the reactor represented, an injection chamber 5 for the liquid to be treated is provided. This chamber 5 is provided, as can be seen in FIG. 2, with a tangential inlet nozzle 6 through which the liquid to be treated enters the reactor. This inlet nozzle 6 ensures a rotational movement of the liquid in the injection chamber 5 which minimizes the loss of entry load and improves the hydraulic distribution of the fluid to be treated.

The liquid exits the injection chamber 5 to enter the active chamber 4 irradiated by the UV radiation, passing through a circular slot 7 forming a necking zone which ensures a loss of load of the order of 5 to 10 times higher than the loss of load upon entry through the injection nozzle 6, thus ensuring homogeneous distribution of the fluid to be treated in the zone of UV irradiation, and thus good homogeneity for the length of stay of each particle entering.

A similar arrangement is provided in the upper part of the reactor in order to further improve the homogeneity of length of stay for each particle of the fluid to be treated in the irradiation zone.

Moreover, the reactor described is also provided at its lower part with means 8 allowing the injection of air under pressure to increase turbulence during the washing of the reactor as described below. A bleeder unit 11 is provided for the upper part of the reactor so as to evacuate the air which has transited it. It should be noted that the invention also covers the possibility of injecting ozone, oxygenated water (or any other reagent capable of completing the disinfection and/or detoxification action of the UV on the liquid being treated), through these injection means 8 provided at the foot of the reactor, thanks to the improvement of photocatalytic activity obtained through UV reflection.

An inlet nozzle on the body of the reactor makes it possible to connect a UV sensor 35 in order to measure the UV transmission coefficient of the liquid wave transiting the active chamber 4 and/or the degree of soiling of the reactor.

A temperature sensor 50 is also provided and gives protection against operation of the UV emitter without the presence of liquid to be treated, which would cause damage.

Figure 3:
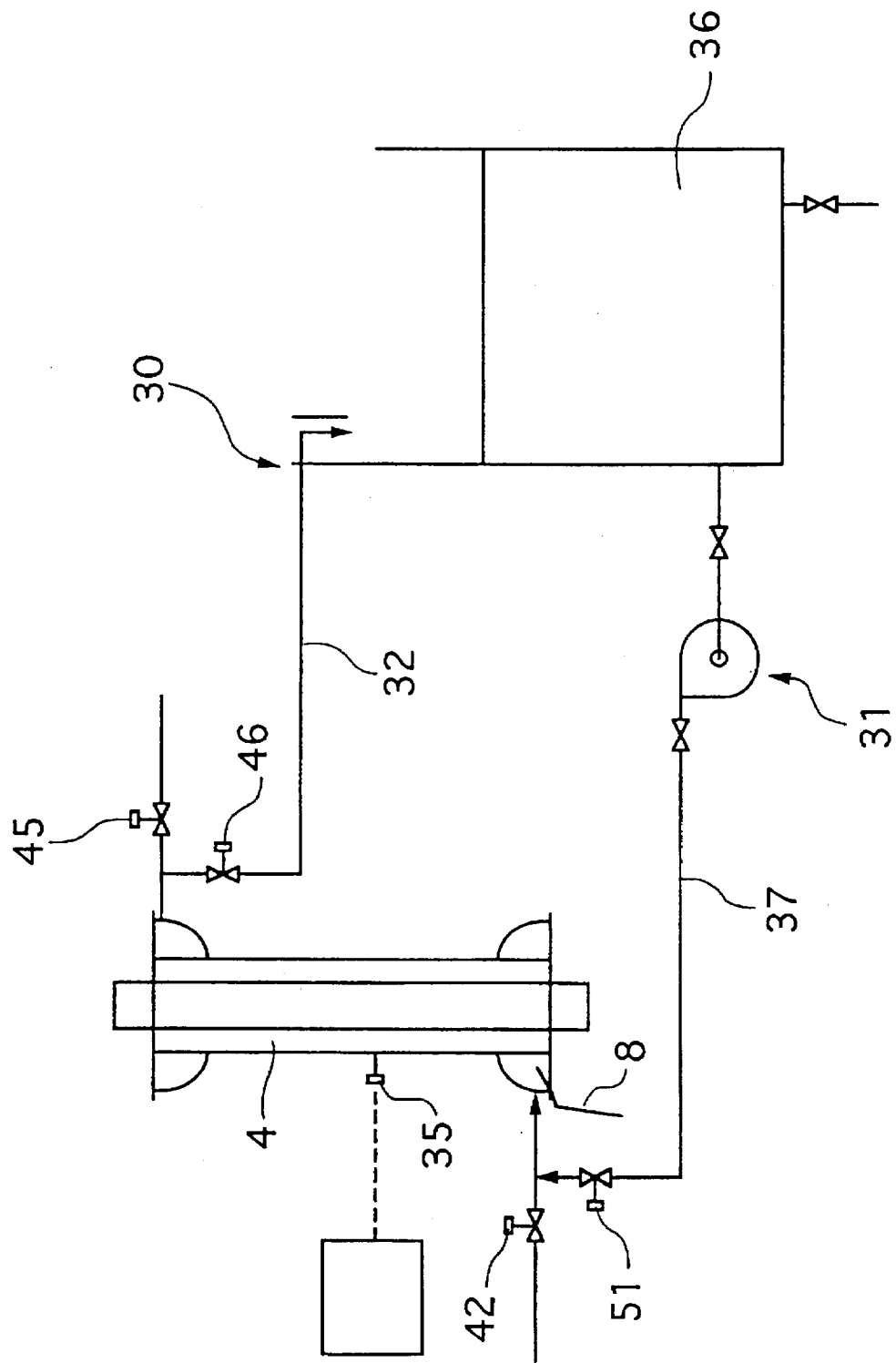
FIG. 3 shows a sectional schematic view of the reactor according to FIGS. 1 and 2, and the washing means of the active chamber thereof.

As can be seen in FIG. 3, the reactor is connected to washing means 30 of chamber 4 of the reactor, making it possible to clean it. These washing means 30 are connected to sensor 35 provided on the reactor and start up as soon as the UV transmission detected by the sensor passes beyond a predetermined threshold. They include a reservoir of washing liquid 36 as well as piping 37 and a pump 31 to supply the washing liquid contained in said reservoir inside the chamber 4 of the reactor. These washing means also include a piping 32 which makes it possible to recycle the washing liquid recuperated at the head of the reactor in reservoir 36.

Depending on the nature and soiling capacity of the liquid treated, the reservoir 36 can be filled with different acid and/or basic chemical products, and/or detergent. It should be noted that one can also, according to other embodiments of the invention, choose to start the washing process according to an established time schedule or manually at more or less regular intervals. It should also be noted that one can plan to heat the cleaning liquid used, for example with an electrical heating element keeping the cleaning liquid in its reservoir at a temperature between 20° C. and 60° C.

Depending on the type of fluid to be treated, generally speaking two types of washing can be provided either separately or in combination:

washing using an acid aqueous solution (diluted phosphoric acid or citric acid for example) especially for the elimination of mineral deposits on the hot walls of the reactor;

washing with an aqueous solution of caustic soda and/or detergents, especially for the elimination of organic deposits.

The efficiency of such washing is greatly improved by the following arrangements, characteristic of the invention:

the mirror polish grain given to the internal face of the wall of the UV reactor, the high turbulence produced by the considerable speeds allowed by the narrow flow section of the reactor, namely 3 cm in the framework of the present example.

the very small internal volume of the reactor (of the order of 30 liters for a reactor of length 1 meter, power 6 kW, for waste water) which allows the recirculation of the reagents with minimum loss for each washing operation. Thus washings can be multiplied without significant consequence in terms of cost of the reagent, while at the same time minimizing the soiling coefficients to be taken into account.

As described above, the efficiency of the washing is also improved by injection of air at the foot of the reactor thanks to injection means 8.

It should be noted that such washing means make it possible to be totally free from the necessity of mechanical washing with scrapers such as those described for example in patents WO 92/22502 or EP 0 467465A1, which are of limited efficiency and not very reliable.

According to the invention, the washing of the reactor can be carried out while the emitter (UV) is operating, thus limiting the aging of the UV emitters which is accelerated during repeated on-off cycles.

When washing is planned, the entry valve 42 is closed and the entry valve for the washing reagent 51 is opened. After evacuation of the initial contents of the reactor of liquid to be treated, the exit valve 45 is closed and, simultaneously, the recycling valve 46 is opened. After washing for the scheduled time in closed circuit, the valve 51 is closed again, the entry valve 42 for the liquid to be treated is opened and, with a programmed delay, the recycling valve 46 is closed and the exit valve 45 for the treated liquid is opened.

According to another procedure designed to minimize consumption of the washing reagent, the UV emitter will be isolated and turned off before washing, and the reactor emptied of its contents of water to be treated before introduction of the cleaning liquid.

The reactor shown in FIGS. 1 to 3 was implemented with waste water with UV transmission of 40 to 46% and a flow of 40 cu.m. per hour and with washing with 5% phosphoric acid every 24 hours. The following results on the reduction of coliform bacteria were obtained:

total coliform bacteria, entry: 1 to 7,107/100 ml
  heat-resistant coliforms, entry: 1 to 6,106/100 ml
  total coliforms, exit (at 5.91 kW): <408 per 100 ml
  heat-resistant coliforms, exit (5.91 kW): <52 per 100 ml.

Figure 4:
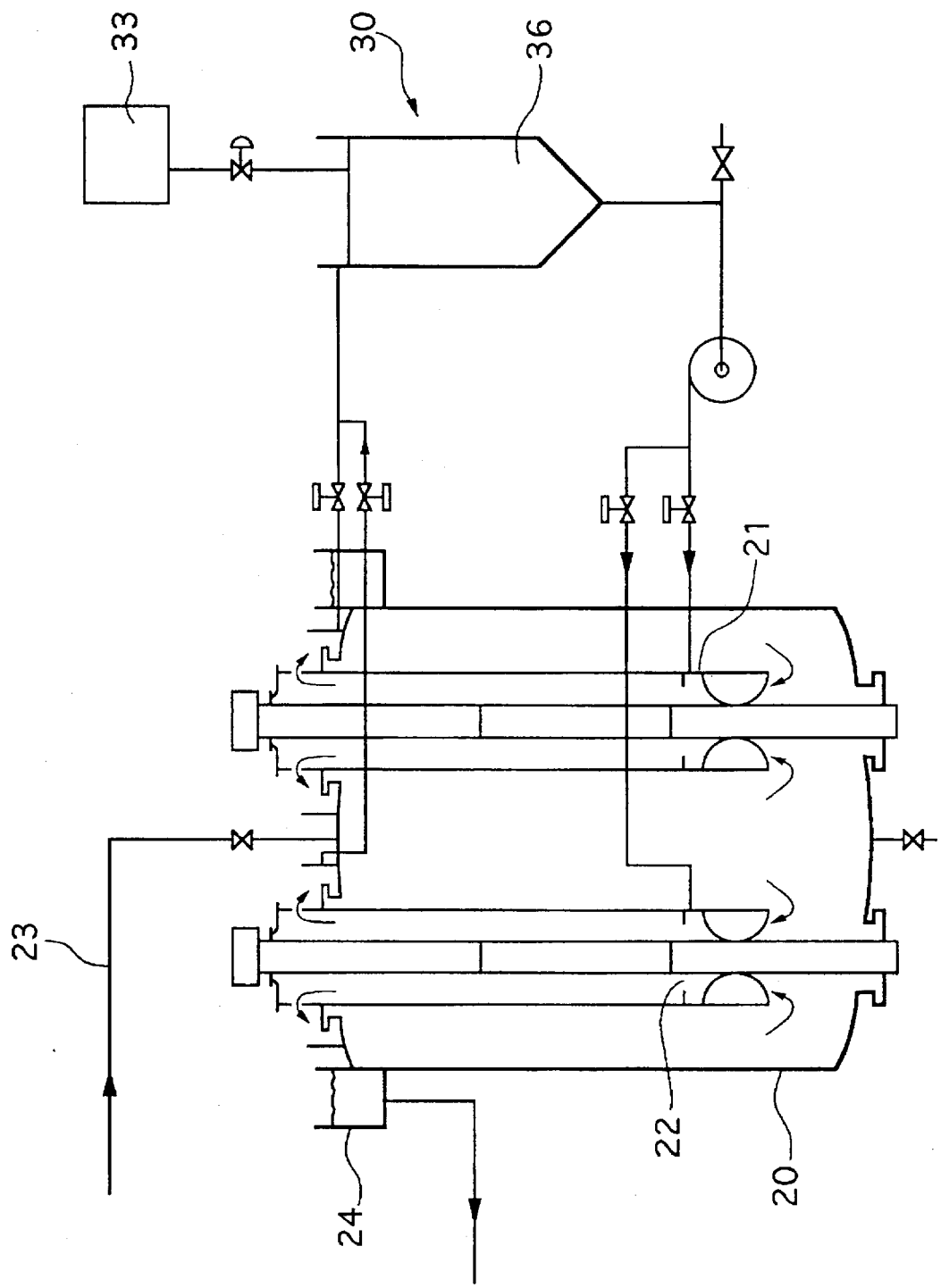
FIG. 4 shows a lateral view of a longitudinal section of a second embodiment of the reactor according to the invention, the installation shown including two reactors positioned in one reservoir.

With reference to FIG. 4, another embodiment of the reactor according to the invention is represented. In this figure, two reactors are placed in a vertical position in a tank 20. In this embodiment, the loss of load upon entry into the reactor is ensured by the symmetric loss of load due to the active part of the reactor (narrow passage 22 between the tubular shell 3 of the reactor and the tubular sheath transparent to UV protecting the emitter), much greater than the asymmetric loss of load engendered by the changes in direction of hydraulic flux in the buffer volume situated under and around the reactors. In this embodiment, the liquid to be treated arrives in the tank 20 through piping 23 and the treated liquid exits the reactors through the peripheral gutters 24 placed at the head of these reactors.

Moreover the installation comprises washing means 30 similar to those of the embodiment shown in FIG. 3 with, in addition, means for readjusting 33 the strength of the cleaning solution contained in the reservoir 36 for example by adding fresh cleaning solution.

Figure 5:
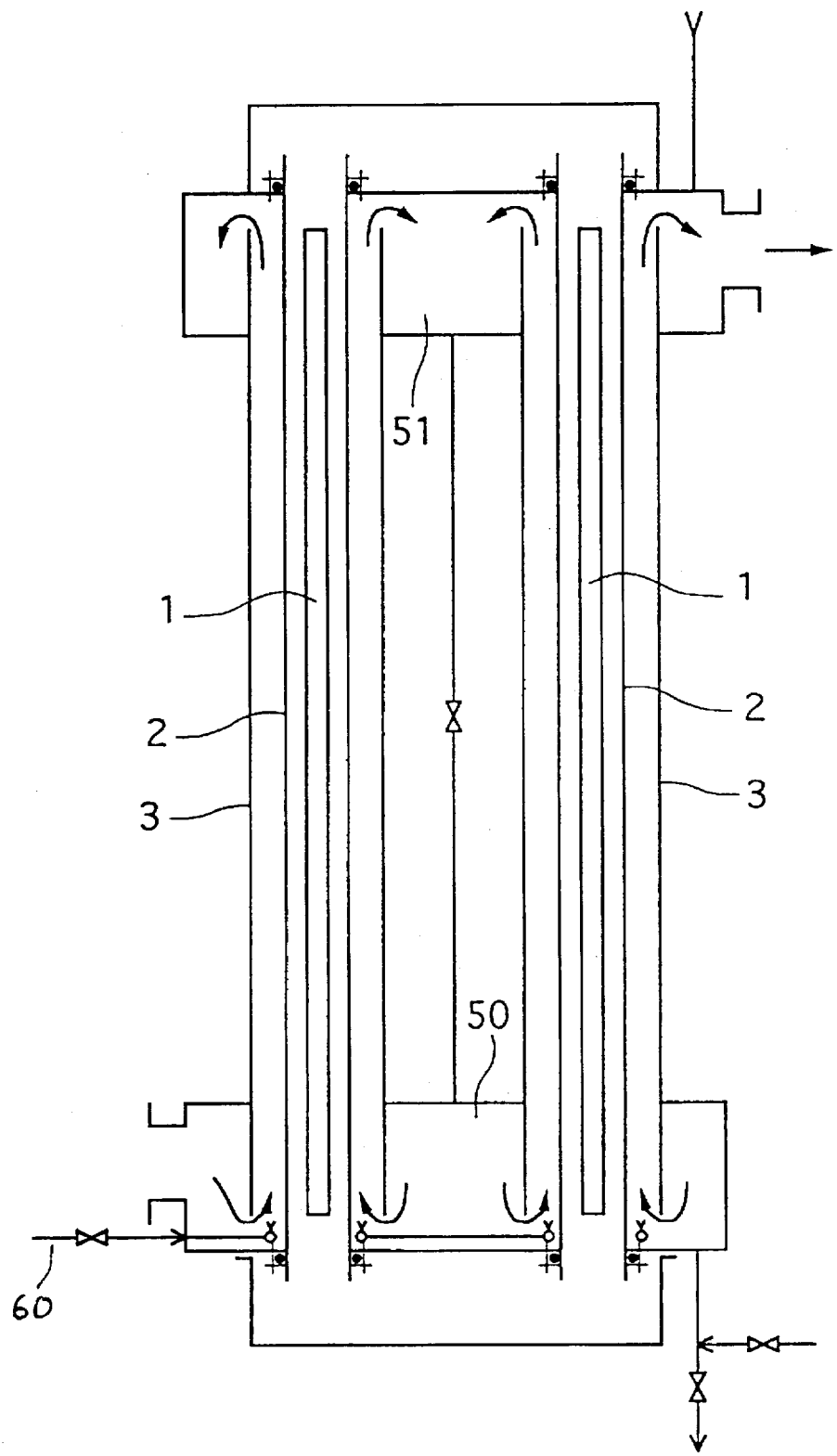
FIG. 5 shows a lateral view of another embodiment, in which several reactors are grouped together (two in the example represented) on common collection chambers.

With reference to FIG. 5, another embodiment of the reactor following the invention is presented.

In this embodiment, the common hydraulic distribution chambers 50 and 51 are made for the inlet and outlet of a series of reactors (here, 2 reactors are represented) each comprising a UV emitter 1, a protective sheath transparent to UV radiation 2, and an internally polished shell 3. The installation also comprises washing means 60.

The embodiments of the invention represented here are not intended to reduce the scope thereof. In particular it should be noted that the UV reactor can be arranged in any position (horizontal, vertical or inclined) except when one wishes to add the possibility of injection of compressed air or reagent gases, which preferably require a vertical position (entry of the fluid to be treated through the lower extremity of the reactor). The number of reactors and washing reagents can also be increased in a way evident to the expert in the art without modification of the operating principle. It should also be noted that several reactors can be put in parallel or in series, by using any hydraulic distribution means which are well known to the expert in the art.

I claim:

1. A UV radiation reactor for treating liquids, comprising:
   at least one high or medium pressure UV radiation emitter arranged coaxially inside a protective sheath transparent to UV to form an assembly installed coaxially inside a tubular shell having an internal face reflecting at least 30% of the UV radiation having a wavelength ranging from 250 nm to 260 nm incident on said internal face, the liquid to be treated flowing in a pipe in an active chamber defined by said internal face of said shell and an external face of said sheath,
   a washing means linked to said active chamber, the washing means adapted to circulate cleaning liquid in said active chamber, an air injector provided upstream from said active chamber to inject air into said cleaning liquid during washing so as to increase turbulence in said cleaning liquid, means to submit the liquid m be treated entering said active chamber to a symmetric loss of load at least three times higher than an asymmetric loss of load observed in the liquid to be treated before entering said reactor, including an injection chamber provided coaxially at one end of said shell and at least one inlet nozzle arranged for introduction of the liquid to be treated into said reactor through said injection chamber, said injection chamber communicating with said active chamber through a circular slot.

2. A reactor as claimed in claim 1, wherein said washing means is adapted and arranged to recycle said cleaning liquid.

3. A reactor as claimed in claim 1, wherein said washing means includes means for readjusting a concentration of said cleaning liquid.

4. A reactor as claimed in claim 1, which includes automatic means for activating said washing means.

5. A reactor as claimed in claim 4, wherein said means for activating include a UV sensor provided at in a wall of said shell of the reactor.

6. A reactor as claimed in claim 1, further comprising means for heating said cleaning liquid.

7. A reactor as claimed in claim 1, wherein said shell is made of stainless steel, said internal face having been subjected to a mirror polish of grain 100 to 350.

8. A reactor as claimed in claim 1, wherein said internal face of said shell comprises a metallic layer obtained by electroplating.

9. A reactor as claimed in claim 1, wherein a dimension of said active chamber is selected so that the Reynolds number of liquid to be treated flowing though said active chamber, where the liquid's density, viscosity and flow rate are known, is greater than 6000.

10. A reactor as claimed in claim 1 further comprising a tank for holding said tubular shell, an annular space being formed between a lower part of said tubular shell and said protective sheath, the annular space being separated from said active chamber by a narrow passage, so as to reduce asymmetric entry of the liquid to be treated into said active chamber.

11. A reactor as claimed in claim 1 which comprises injection means for injecting at least one reagent to treat said liquid, said injection means being provided upstream from said active chamber.

12. A reactor as claimed in claim 1 further comprising a regulator to regulate power of said emitter as a function of one or more parameters chosen from the group consisting of flow rate of treated liquid, UV transmission of the treated liquid, and a length of time since a previous washing.

13. A reactor as claimed in claim 1, wherein said at least one nozzle is arranged for tangential introduction of the liquid into said reaction chamber.

* * * * *